United States Patent
Harms et al.

(10) Patent No.: US 10,543,321 B2
(45) Date of Patent: Jan. 28, 2020

(54) PEN CAP

(75) Inventors: Michael Harms, Frankfurt am Main (DE); Steffen Raab, Frankfurt am Main (DE)

(73) Assignee: Sanofi-Aventis Deutschland GmbH, Frankfurt am Main (DE)

(*) Notice: Subject to any disclaimer, the term of this patent is extended or adjusted under 35 U.S.C. 154(b) by 145 days.

(21) Appl. No.: 13/258,168

(22) PCT Filed: Mar. 31, 2010

(86) PCT No.: PCT/EP2010/054347
§ 371 (c)(1),
(2), (4) Date: Mar. 12, 2012

(87) PCT Pub. No.: WO2010/115821
PCT Pub. Date: Oct. 14, 2010

(65) Prior Publication Data
US 2012/0165746 A1    Jun. 28, 2012

Related U.S. Application Data

(60) Provisional application No. 61/169,869, filed on Apr. 16, 2009.

(30) Foreign Application Priority Data

Mar. 31, 2009  (EP) .................................... 09004670

(51) Int. Cl.
*A61M 5/32*   (2006.01)
*A61M 5/31*   (2006.01)

(52) U.S. Cl.
CPC ......... *A61M 5/3202* (2013.01); *A61M 5/3213* (2013.01); *A61M 2005/3104* (2013.01)

(58) Field of Classification Search
CPC ................. A61M 5/3202; A61M 5/50; A61M 2005/3215; A61M 5/3213;
(Continued)

(56) References Cited

U.S. PATENT DOCUMENTS 533,575 A    2/1895  Wilkens
3,545,607 A *  12/1970  Keller .................... A61M 5/28
                                                                    206/365
(Continued)

FOREIGN PATENT DOCUMENTS

CA    2138528 C    12/1998
CA    2359375 A1    7/2000
(Continued)

OTHER PUBLICATIONS

International Preliminary Report on Patentability for International App. No. PCT/EP2010/054347, dated Oct. 4, 2011.
(Continued)

*Primary Examiner* — Amber R Stiles
*Assistant Examiner* — Laura C Schell
(74) *Attorney, Agent, or Firm* — McCarter & English, LLP

(57) ABSTRACT

The present invention refers to a pen cap, being capable of covering a distal end of a drug delivery device comprising at least one protruding element located inside the pen cap which prevents that the rim of an outer needle cap, while being a protective casing for the needle at the distal end of the drug delivery device, can get stuck within a part of the pen cap if the user puts the pen cap on the drug delivery device. The inner diameter of the pen cap is reduced by means of the at least one protruding element, such that the inner diameter of the pen cap is smaller than the largest outer diameter of the outer needle cap. Furthermore, the invention
(Continued)

relates to a drug delivery device comprising a pen cap with the described protruding elements.

14 Claims, 2 Drawing Sheets

(58) Field of Classification Search
CPC .... A61M 2005/3104; A61M 2005/312; A61M 2005/247; A61M 2005/2474; A61M 5/3204; A61M 5/20–2005/2093; A61M 5/3293; A61M 5/347; A61M 2205/586; A61B 12/006
USPC .................................. 604/263, 241, 242, 243
See application file for complete search history.

(56) References Cited

U.S. PATENT DOCUMENTS

| | | | |
|---|---|---|---|
| 4,317,446 A * | 3/1982 | Ambrosio et al. ............ 604/193 | |
| 4,624,660 A * | 11/1986 | Mijers ................. A61M 5/2033 | |
| | | | 604/136 |
| 4,636,201 A * | 1/1987 | Ambrose et al. ............ 604/192 | |
| 4,654,034 A * | 3/1987 | Masters .............. A61M 5/3271 | |
| | | | 604/192 |
| 4,742,910 A * | 5/1988 | Staebler .............. A61M 5/3213 | |
| | | | 206/365 |
| 4,865,591 A | 9/1989 | Sams | |
| 4,986,817 A * | 1/1991 | Code ................... A61M 5/3213 | |
| | | | 604/192 |
| 5,092,842 A | 3/1992 | Bechtold et al. | |
| 5,098,400 A * | 3/1992 | Crouse ................ A61M 5/3213 | |
| | | | 604/192 |
| 5,147,325 A * | 9/1992 | Mitchell ............. A61M 5/3213 | |
| | | | 604/192 |
| 5,226,895 A | 7/1993 | Harris | |
| 5,226,896 A | 7/1993 | Harris | |
| 5,279,586 A | 1/1994 | Balkwill | |
| 5,304,152 A | 4/1994 | Sams | |
| 5,320,609 A | 6/1994 | Haber et al. | |
| 5,378,233 A | 1/1995 | Haber et al. | |
| 5,383,865 A | 1/1995 | Michel | |
| 5,391,157 A | 2/1995 | Harris et al. | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,807,346 A | 9/1998 | Frezza | |
| 5,820,602 A | 10/1998 | Kovelman et al. | |
| 5,851,079 A | 12/1998 | Horstman et al. | |
| 5,921,966 A | 7/1999 | Bendek et al. | |
| 5,941,857 A * | 8/1999 | Nguyen et al. ............... 604/263 | |
| 5,957,896 A | 9/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,562,006 B1 | 5/2003 | Hjertman et al. | |
| 6,613,023 B2 | 9/2003 | Kirchhofer et al. | |
| 6,699,224 B2 | 3/2004 | Kirchhofer et al. | |
| 6,899,698 B2 | 5/2005 | Sams | |
| 6,932,794 B2 | 8/2005 | Giambattista et al. | |
| 6,936,032 B1 | 8/2005 | Bush, Jr. et al. | |
| 7,169,132 B2 | 1/2007 | Bendek et al. | |
| 7,241,278 B2 | 7/2007 | Moller | |
| 7,678,084 B2 | 3/2010 | Judson et al. | |
| 7,850,662 B2 | 12/2010 | Veasey et al. | |
| 8,133,202 B2 * | 3/2012 | Marsh ........................... 604/117 | |
| 8,187,233 B2 | 5/2012 | Harms et al. | |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0097883 A1 | 5/2004 | Roe | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0153693 A1 | 7/2006 | Fiechter et al. | |
| 2007/0016143 A1 | 1/2007 | Miller et al. | |
| 2009/0069753 A1 * | 3/2009 | Ruan et al. ................... 604/192 | |
| 2009/0118678 A1 * | 5/2009 | Kawashima ........ A61M 5/3213 | |
| | | | 604/197 |
| 2009/0275916 A1 | 11/2009 | Harms et al. | |
| 2012/0016300 A1 * | 1/2012 | Ruan ............................ 604/110 | |

FOREIGN PATENT DOCUMENTS

| | | | |
|---|---|---|---|
| EP | 0496141 A1 | 7/1992 | |
| EP | 0554995 | 8/1993 | |
| EP | 0897729 A2 | 2/1999 | |
| EP | 0903157 | 3/1999 | |
| EP | 0937471 A2 | 8/1999 | |
| EP | 0937476 A2 | 8/1999 | |
| EP | 1007115 | 6/2000 | |
| EP | 1776975 A2 | 4/2007 | |
| EP | 1923085 | 5/2008 | |
| EP | 2033672 | * | 3/2009 |
| WO | 93/07922 A1 | 4/1993 | |
| WO | 93/24160 A1 | 12/1993 | |
| WO | 99/38554 A1 | 8/1999 | |
| WO | 01/10484 A1 | 2/2001 | |
| WO | 02/030495 A2 | 4/2002 | |
| WO | 02/092153 A2 | 11/2002 | |
| WO | 03/080160 A1 | 10/2003 | |
| WO | 2006/084876 A1 | 8/2006 | |
| WO | 2008/067467 | 6/2008 | |

OTHER PUBLICATIONS

European Search Report for EP Patent Application No. 09004670 dated Aug. 21, 2009.
International Search Report for PCT Patent Application No. PCT/EP2010/054347, dated Jul. 13, 2010.
ISO—International Organization for Standarization, Pen-injectors for medical use, Part 1: Pen-injectors—Requirements and test methds. ISO 11608-1, First Edition, 32 pages, Dec. 15, 2000.
ISO—International Organization for Standarization, Pen-injectors for medical use, Part 2: Needles—Requirements and test methods. ISO 11608-2, First Edition, 18 pages, Dec. 15, 2000.
ISO—International Organization for Standarization, Pen-injectors for medical use, Part 3: Finished cartridges—Requirements and test methods. ISO 11608-3, First Edition, 22 pages, Dec. 15, 2000.

* cited by examiner

PEN CAP

CROSS REFERENCE TO RELATED APPLICATIONS

The present application is a U.S. National Phase Application pursuant to 35 U.S.C. § 371 of International Application No. PCT/EP2010/054347 filed Mar. 31, 2010, which claims priority to European Patent Application No. 09004670.7 filed on Mar. 31, 2009 and U.S. Provisional Patent Application No. 61/169,869 filed Apr. 16, 2009. The entire disclosure contents of these applications are herewith incorporated by reference into the present application.

FIELD OF INVENTION

The present invention relates to a pen cap which is used for covering the distal end of a drug delivery device. Furthermore, the present invention relates to a drug delivery device comprising a pen cap.

BACKGROUND

Drug delivery devices which comprise a removable pen cap are known for example from EP 1 007 115 B1.

Drug delivery devices are to be used in case of a disease where a permanent medication is needed, like for example diabetes. These devices are very comfortable in usage for self-administration of insulin or other medicinal products by a patient. Some reusable pen-type injectors are described in EP 1 923 085 A1 or in EP 0 554 995 A1.

SUMMARY

It is an aim of the present invention to provide an improved pen cap for a drug delivery device and therefore an improved drug delivery device.

According to a first aspect of the present invention, a pen cap is provided that is capable of covering a distal end of a drug delivery device, the drug delivery device being adapted to carry a needle at its distal end, the needle being covered by an outer needle cap as a protective casing in a non-use condition. The pen cap may comprise at least one protruding element. The at least one protruding element located inside the pen cap may be adapted and arranged to prevent that the outer needle cap gets stuck within a part of the pen cap when a user mounts the pen cap on the drug delivery device.

In a preferred embodiment, the pen cap has a closed end as well as an open end facing in the opposite direction. At least one protruding element is located inside the pen cap.

The distal end of the drug delivery device is provided with a needle which is covered by an outer needle cap forming a protective casing for the needle. While being a protective casing for the needle at the distal end of the drug delivery device the at least one protruding element inside the pen cap prevents the outer needle cap from getting stuck within the pen cap when the user puts the pen cap on the drug delivery device.

The proximal end of the outer needle cap provides a rim. The inventors have identified that in many cases the rim of the outer needle cap has a diameter that mostly fits into the opening at the open end of the pen cap. When the user puts the pen cap on the drug delivery device it may occur that the rim of the outer needle cap gets jammed within the pen cap. In case the pen cap has at least partly a conic shape with the opening of the cone being directed towards the open end of the cap, the jamming risk is particularly high.

The protruding elements are shaped and sized in such a way that the inner diameter of the pen cap is smaller than the diameter of the rim of the outer needle cap. In a preferred embodiment this is true for all available needle units that fit to the drug delivery device.

In a preferred embodiment, at least one protruding element extends along the longitudinal axis of the pen cap.

The protruding element can extend from the closed end to the open end of the pen cap. As an alternative, the protruding element may be shorter than the pen cap and a leading edge of the protruding element is retracted with regard to the open end of the pen cap.

In any case the rim of the outer needle cap abuts the leading edge of the protruding element while the outer needle cap is inserted in the pen cap.

In a preferred embodiment one end of the at least one protruding element is arranged at the open end of the pen cap.

In a particularly preferred embodiment as seen along the at least one protruding element from its proximal end to its distal end at least one inwardly directed step is provided in the pen cap.

The stepped shape can be provided by arranging at least one stepped protruding element inside the pen cap. The step is radially inwardly directed. The step may divide the region of the pen cap, where the at least one protruding element is arranged, into two parts with different inner diameters. The part with the smaller inner diameter is located in the distal region of the pen cap.

Possibilities to achieve a configuration with smaller diameter in the distal region of the pen cap are given by two stepped protruding elements arranged at opposite sides of the pen cap or by two ring-shaped protruding elements with different inner diameters.

By having different inner diameters with the smallest inner diameter at the distal end of the pen cap, it can be avoided that most commercially available needle units which may comprise different diameters of the outer needle cap can get stuck during insertion in the pen cap.

According to a preferred embodiment of the present invention the at least one protruding element arranged inside the pen cap is a bar.

According to further preferred embodiments, the number and the shape of the protruding elements may vary. In case that a number of two protruding elements is provided, the elements can be arranged for example at opposite sides of the pen cap. In the case of three elements the elements can be arranged in equiangular positions such that they form the corners of an equilateral triangle. In case even more protruding elements are provided, they can form the shape of a ring-like protrusion.

In another preferred embodiment at least one protruding element is a ring.

It is possible to arrange the ring near the open end of the pen cap. Another possibility is to arrange the ring in a small distance to the open end of the pen cap.

According to another preferred embodiment the ring is located directly at the open end of the cap.

In one embodiment the at least one protruding element is made of plastic.

In another embodiment the at least one protruding element is made of metal.

According to another preferred embodiment the at least one protruding element is molded into the cap.

One possible method of manufacturing a pen cap according to the present invention is injection molding. This is particularly preferred in case that the pen cap is made of plastic. In this case, injection molding provides an easy method to manufacture the pen cap and the protruding element in one single process.

In one embodiment the inner diameter of the pen cap is reduced by means of at least one protruding element, such that the inner diameter of the pen cap is smaller than the largest outer diameter of the outer needle cap.

By providing at least one protruding element inside the pen cap, the inner diameter of the pen cap is reduced. The dimension, in particular the radial dimension of the at least one protruding element depends on the reduction of the inner diameter of the pen cap which is required in order to prevent sticking of the outer needle cap in the pen cap.

According to another embodiment a drug delivery device is provided wherein the inner diameter of the pen cap near the open end of the pen cap is reduced by means of at least one protruding element, such that the inner diameter of the pen cap is smaller than the largest outer diameter of the outer needle cap. The outer needle cap may have its largest outer diameter at the position where the rim is located.

According to a preferred embodiment, a pen cap is provided being capable of covering a distal end of a drug delivery device, the drug delivery device being adapted to carry a needle at its distal end, the needle being covered by an outer needle cap as a protective casing in a non-use condition. The pen cap comprises at least one protruding element located inside the pen cap which prevents that the outer needle cap gets stuck within a part of the pen cap when a user mounts the pen cap on the drug delivery device.

BRIEF DESCRIPTION OF THE FIGURES

In the following the invention is described in further details with references to the drawings, wherein.

Identical reference signs denote identical or comparable components.

DETAILED DESCRIPTION

Figure 1:
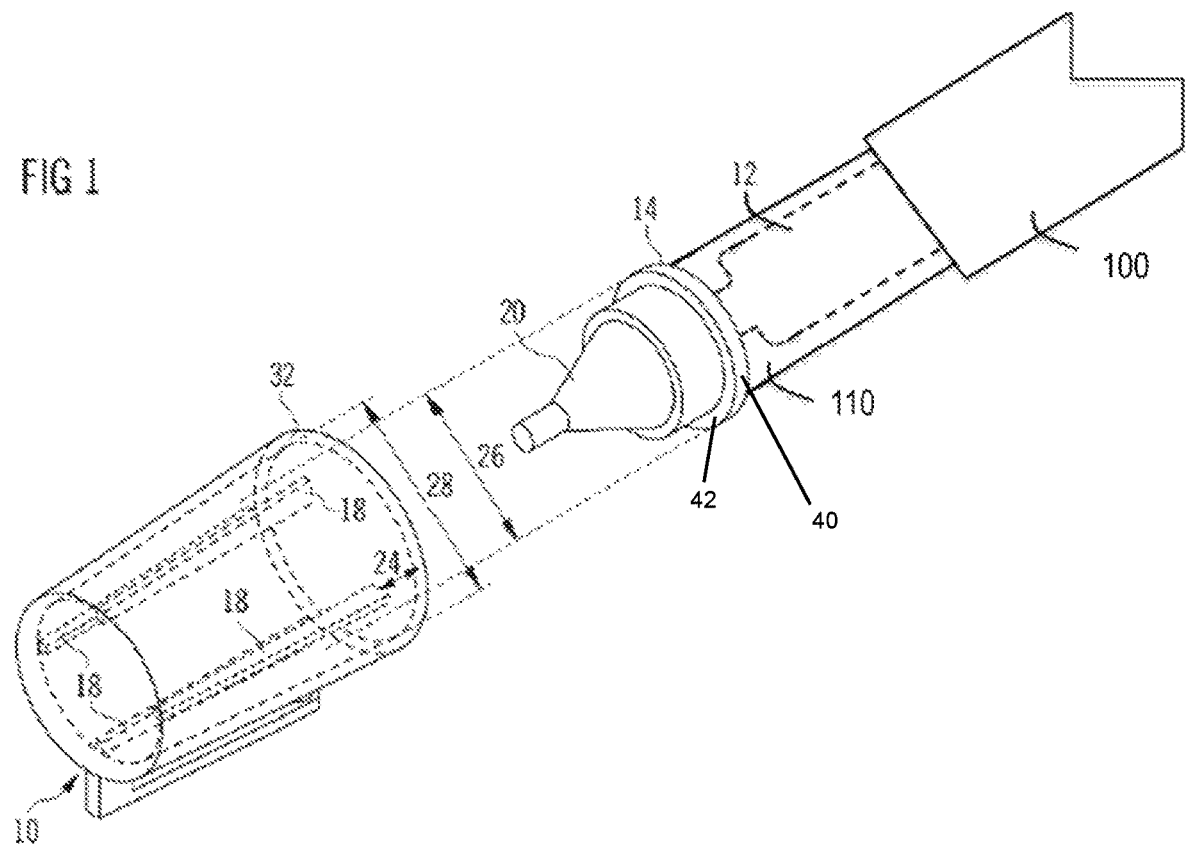
FIG. 1 shows the distal end of a drug delivery device comprising the housing with an outer needle cap on top of a needle unit and the pen cap with the protruding elements.

In the embodiment shown in FIG. 1 the housing 100 of a drug delivery device comprises a cartridge holder 110 wherein a cartridge 12 containing a medicinal product is located. The term "medicinal product", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (AC S), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38 Exendin-4(1-39)-NH2,
H-(Lys)6-des Pro36, Pro38 [Asp28] Exendin-4(1-39)-NH2, H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

An outer needle cap 20 is located at the distal end of the drug delivery device. This outer needle cap 20 covers a sterile needle unit which in turn is covered by an inner needle cap not explicitly shown in FIG. 1. The outer needle cap 20 comprises a distal and a proximal end which are both formed cylindrically. The diameter of the distal cylindrical part is smaller than the diameter of the proximal cylindrical part. The proximal cylindrical part of the outer needle cap 20 is limited by a rim 14. The rim 14 may include a radially outward facing surface 40 and a distal surface 42, as shown in FIG. 1. This rim 14 forms the part of the outer needle cap 20 with the largest diameter. A connecting part is arranged between the distal end of the cylindrical part with the larger diameter and the proximal end of the cylindrical part with the smaller diameter.

Inside the conic shaped pen cap 10, protruding elements 18 are arranged to prevent that the rim 14 of the outer needle cap 20 gets stuck within the pen cap 10 when the outer needle cap 20 is inserted in the pen cap 10. Each protruding element 18 is bar-shaped and arranged along the longitudinal axis of the pen cap 10 and extends between the proximal and the distal end of the pen cap 10. The leading edges of the protruding elements are located at a distance 24 from the open end of the pen cap 10.

The size and shape of the protruding elements 18 were chosen in such a way that the inner diameter 30 of the pen cap is smaller than the outer diameter 26 of the rim of the outer needle cap 20. Here the inner diameter 30 of the pen cap 10 is limited by the inner ends of the protruding elements.

By trying to insert the outer needle cap 20 into the pen cap 10 the surface of the rim 14 of the outer needle cap 20 will mechanically cooperate with, in particular abut, the leading edges of each of the four protruding elements 18 shown in FIG. 1. As such, it is prevented that the distal end of the drug delivery device with an outer needle cap 20 on top of the needle is fully inserted into the pen cap 10 and gets stuck within the pen cap 10. This is possible, because of the fact that the outer diameter of the rim 14 at the proximal end of the outer needle 20 cap is smaller than the inner diameter 28 at the open end of the pen cap.

Figure 2:
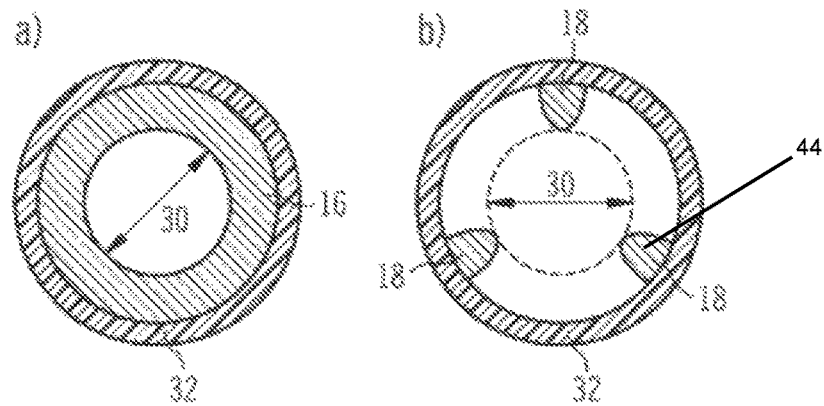
FIG. 2a shows a top view of the open end of the pen cap comprising a ring-shaped protruding element.
FIG. 2b shows a top view of the open end of the pen cap comprising three bar-shaped protruding elements.

FIG. 2a shows a top view of the open end of a pen cap 32 with a ring-shaped protruding element 16 inside the pen cap 10. This ring-shaped element 16 is located near the open end of the pen cap 32. This ring-shaped protruding element narrows the inner diameter 30.

FIG. 2b shows a top view of the open end of the pen cap 32 with three bar-shaped protruding elements 18 arranged along the longitudinal axis between the proximal and the distal end of the pen cap 10. These three bar-shaped protruding elements 18 narrow the inner diameter 30. In an exemplary embodiment, the at least one protruding element 18, as taught herein, may include a proximal end surface 44, as shown in FIG. 2b.

Figure 3:
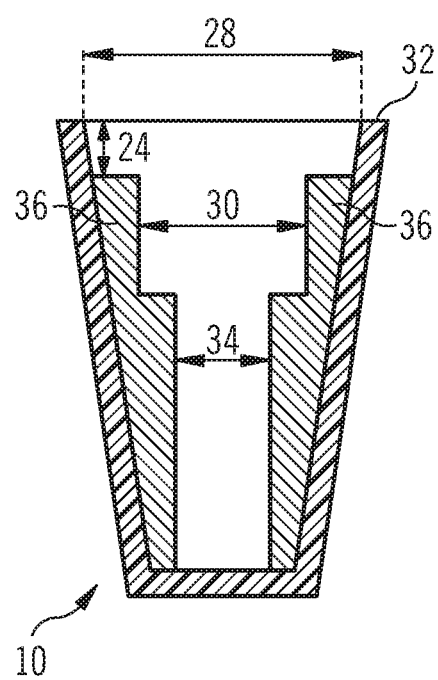
FIG. 3 shows a cross sectional view of the pen cap, the pen cap comprising two stepped protruding elements.

FIG. 3 shows a cross sectional view of a pen cap 10 with two stepped protruding elements 36 arranged at opposite sides of the pen cap 10. The two stepped protruding elements 36 are arranged in a distance 24 to the open end of the pen cap 32. The inner diameter of the pen cap 28 at the open end is reduced by the two protruding elements. The inner diameter in the distal region of the pen cap 34 is smaller than the inner diameter 30 in the proximal region of the protruding elements 36. The inner diameter in the distal region of the pen cap 34 should be greater than the outer diameter of a tapered cartridge or cartridge holder, which is not shown in the figure. The cartridge or cartridge holder may thus be still inserted into the pen cap 10 while most commercially available outer needle caps 20 are reliably prevented from getting stuck in the pen cap 10.

The present examples and embodiments are to be considered as illustrative and not restrictive, and the invention is not to be limited to the details given herein, but may be modified within the scope and equivalence of the appended claims.

The invention claimed is:

1. A drug delivery device and pen cap combination comprising:
   a housing having an attached cartridge holder that contains a cartridge of medicinal product; and
   a pen cap having an open proximal end and a closed distal end, the pen cap configured for attachment to the drug delivery device,
   wherein an outer needle cap is configured for attachment to a distal end of the cartridge holder, wherein the outer needle cap completely covers a needle and provides a protective casing for the needle in a non-use condition, where the outer needle cap includes a rim having a radially outward facing surface and a distal surface, an outer diameter of the rim defining a maximum outer diameter of the outer needle cap,
   wherein the pen cap has an inner diameter defined by an inner wall at the open proximal end of the pen cap, wherein the pen cap comprises at least one protruding element located inside the pen cap that protrudes from the inner wall, wherein the at least one protruding element is elongate, has a proximal end and a distal end, and has a proximal end surface that faces the open proximal end of the pen cap, the proximal end surface of the at least one protruding element being oriented perpendicular to a longitudinal axis of the pen cap, and being recessed from a proximal end of the inner wall of the open proximal end of the pen cap, wherein the proximal end of the at least one protruding element results in a first diameter of the pen cap that is smaller than the maximum outer diameter of the outer needle cap,
   wherein the first diameter is narrower than the inner diameter of the pen cap,
   wherein the distal surface of the rim of the outer needle cap abuts the proximal end surface of the at least one protruding element of the pen cap when the outer needle cap is inserted into the pen cap, and wherein at least a portion of the radially outward facing surface of the rim is covered by the pen cap when the distal surface of the rim abuts the proximal end surface of the at least one protruding element, and
   wherein the abutment of the distal surface of the rim and the proximal end surface of the at least one protruding element blocks the distal surface of the rim from being advanced into the pen cap beyond the proximal end surface of the at least one protruding element and prevents the outer needle cap attached to the drug delivery device from being advanced sufficiently distally into the pen cap such that the outer needle cap becomes stuck within the pen cap when a user mounts the pen cap on the drug delivery device.

2. The drug delivery device and pen cap combination according to claim 1, wherein the at least one protruding element extends along the longitudinal axis of the pen cap.

3. The drug delivery device and pen cap combination according to claim 1, wherein the at least one protruding element includes at least one inwardly directed step along the length of the at least one protruding element, the at least one inwardly directed step provided between the proximal end and the distal end of the at least one protruding element.

4. The drug delivery device and pen cap combination according to claim 1, wherein the at least one protruding element is a bar.

5. The drug delivery device and pen cap combination according to claim 1, wherein the at least one protruding element is a ring.

6. The drug delivery device and pen cap combination according to claim 1, wherein the at least one protruding element comprises two protruding elements, and wherein the two protruding elements are located at opposite sides of the pen cap.

7. The drug delivery device and pen cap combination according to claim 1, wherein the at least one protruding element is made of plastic.

8. The drug delivery device and pen cap combination cap according to claim 1, wherein the at least one protruding element is made of metal.

9. The drug delivery device and pen cap combination according to claim 1, wherein the at least one protruding element is molded into the pen cap.

10. The drug delivery device and pen cap combination according to claim 1, wherein the medicinal product is a pharmaceutical formulation containing a pharmaceutically active compound, the pharmaceutically active compound comprising at least one human insulin or a human insulin analogue or derivative, glucagon-like peptide (GLP-1) or an analogue or derivative thereof, or exedin-3 or exedin-4 or an analogue or derivative of exedin-3 or exedin-4.

11. The drug delivery device and pen cap combination according to claim 1, wherein the at least one protruding element extends from the recessed proximal end surface to the closed distal end of the pen cap.

12. The drug delivery device and pen cap combination according to claim 1, wherein a cross-sectional area of the proximal end of the at least one protruding element is greater than a cross-sectional area of the distal end of the at least one protruding element.

13. The drug delivery device and pen cap combination according to claim 1, wherein the at least one protruding element of the pen cap comprises three protruding elements, and wherein the three protruding elements are circumferentially spaced approximately equidistantly from one another along the inner wall of the pen cap.

14. The drug delivery device and pen cap combination according to claim 1, the proximal end surface of the at least one protruding element being located longitudinally at a most proximal location of the at least one at least one protruding element.

* * * * *

UNITED STATES PATENT AND TRADEMARK OFFICE
CERTIFICATE OF CORRECTION

PATENT NO. : 10,543,321 B2  
APPLICATION NO. : 13/258168  
DATED : January 28, 2020  
INVENTOR(S) : Michael Harms et al.

Page 1 of 1

It is certified that error appears in the above-identified patent and that said Letters Patent is hereby corrected as shown below:

In the Claims

At Column 8, Claim number 8, Line number 33, delete "pen cap combination cap", and replace with --pen cap combination--.

At Column 8, Claim number 14, Line number 65, delete "at least one at least one", and replace with --at least one--.

Signed and Sealed this
Thirtieth Day of June, 2020

Andrei Iancu
*Director of the United States Patent and Trademark Office*